(12) United States Patent
Yao et al.

(10) Patent No.: US 10,207,962 B2
(45) Date of Patent: *Feb. 19, 2019

(54) OLIGOMERIZATION OF ETHYLENE TO LIQUID TRANSPORTATION FUELS WITH POST SYNTHESIS TREATED ZSM-5 CATALYST

(71) Applicant: PHILLIPS 66 COMPANY, Houston, TX (US)

(72) Inventors: Jianhua Yao, Bartlesville, OK (US); Bruce B. Randolph, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/216,330

(22) Filed: Jul. 21, 2016

(65) Prior Publication Data

US 2018/0022664 A1    Jan. 25, 2018

(51) Int. Cl.
*C07C 2/12* (2006.01)
*B01J 29/40* (2006.01)
*C01B 39/38* (2006.01)
*C01B 39/02* (2006.01)

(52) U.S. Cl.
CPC ............... *C07C 2/12* (2013.01); *B01J 29/40* (2013.01); *C01B 39/026* (2013.01); *C01B 39/38* (2013.01); *C07C 2529/40* (2013.01); *C10L 2200/0423* (2013.01); *C10L 2270/023* (2013.01)

(58) Field of Classification Search
CPC ....... C07C 15/00; C07C 2/00; C07C 2529/40; C07C 2/02; C10G 50/00
See application file for complete search history.

(56) References Cited

U.S. PATENT DOCUMENTS

| | | | |
|---|---|---|---|
| 5,043,499 A * | 8/1991 | Harandi | C10G 50/00 585/301 |
| 5,827,422 A | 10/1998 | Drake et al. | |
| 5,952,259 A | 9/1999 | Drake et al. | |
| 9,580,329 B2 * | 2/2017 | Li | C01B 39/026 |
| 2014/0275669 A1 * | 9/2014 | Daage | B01J 29/40 585/251 |

OTHER PUBLICATIONS

Amin, Nor Aishah Saidina, Dealuminated ZSM-5 Zeolite Catalyst for Ethylene Oligomerization to Liquid Fuels, Journal of Natural Gas Chemistry, 2002, 79-86, 11, Science Press.

* cited by examiner

*Primary Examiner* — Sharon Pregler
(74) *Attorney, Agent, or Firm* — Phillips 66 Company

(57) ABSTRACT

A process for post synthesis treatment of ZSM-5 catalyst for converting ethylene to liquid fuel products providing substantially improved catalyst life. The treatment comprises either a base treatment, an acid treatment or a two-step treatment where one is with an acid and the other is with a base. The base treatment is provided by a weak sodium hydroxide such as less than 1 Molar concentration. The acid treatment is stronger acid where, for example, a hydrogen chloride solution at greater than 2 Molar concentration is used.

14 Claims, 2 Drawing Sheets

OLIGOMERIZATION OF ETHYLENE TO LIQUID TRANSPORTATION FUELS WITH POST SYNTHESIS TREATED ZSM-5 CATALYST

CROSS-REFERENCE TO RELATED APPLICATIONS

None.

STATEMENT REGARDING FEDERALLY SPONSORED RESEARCH OR DEVELOPMENT

None.

FIELD OF THE INVENTION

This invention relates to converting light alkanes to fuel and especially to improved catalysts for the economic and practical implementation of a commercial conversion process.

BACKGROUND OF THE INVENTION

The US shale gas boom has resulted in a significant increase in natural gas production as well as a significant increase in the production of natural gas liquids. One of the main components of the natural gas liquids produced with natural gas is ethane. Ethane is most commonly used as petrochemical feedstock such as for the production of ethylene. Ethylene is a feedstock for many, many high volume chemical based products such as polyethylene and styrene plastics, among many others. However, there are no other sizable consumption markets for ethane. US ethane supplies currently exceed demand by about 300,000 barrels per day causing depressed prices for ethane and attracting considerable investment into new ethane to ethylene production facilities. Most supply/demand estimates indicate that ethane will remain in surplus for many years and these predictions take in to account the new ethane to ethylene conversion capacity being built. Therefore, new markets for ethane and new technologies for converting ethane to products that have large existing or substantially growing demand would be very attractive in light of the projected low prices for ethane for many years. One of the largest end use markets is liquid transportation fuel and a simple conversion technology to any transportation fuel could prove to be quite profitable.

So, with the expectation that ethane will be plentiful and cheap, old technologies are being reconsidered that use ethane as a feedstock. One old technology is the conversion of ethane to current fuel markets such as gasoline and/or diesel. However, while there are known chemical processes for converting ethane to gasoline and or diesel, it has yet to be put into commercial production. With excess ethane currently being produced, there is or will soon be a need to create commercially viable processes to convert ethane to liquid transportation fuels.

BRIEF SUMMARY OF THE DISCLOSURE

The invention more particularly relates to oligomerizing ethylene to transportation fuel products in a reactor with a fixed bed of ZSM 5 catalyst that is essentially free of catalyst metals other than silica and alumina. The ZSM 5 catalyst has been provided with post synthesis, two-step treatment of an acid wash and a base wash to resist coke formation in the zeolite crystallites and extend catalyst life. The oligomerizing is conducted at a pressure between 0 psig and 800 psig, a temperature of between 260° C. and 420° C., and a gas hourly space velocity of between 1000 and 5000 inverse hours and wherein at least 85% of the ethylene is converted.

The invention also relates to oligomerizing ethylene to transportation fuel products in a reactor with a fixed bed of ZSM 5 catalyst that is essentially free of catalyst metals other than silica and alumina. The ZSM 5 catalyst has been provided with post synthesis base acid treatment to resist coke formation in the zeolite crystallites and extend catalyst life. The oligomerizing is conducted at a pressure between 0 psig and 800 psig, a temperature of between 260° C. and 420° C., and a gas hourly space velocity of between 1000 and 5000 inverse hours wherein at least 85% of the ethylene is converted. The post synthesis treatment of the catalyst is a multi-step process where a base treatment is performed first with sodium hydroxide at between about 0.0075 and about 0.15 Molar concentration and at a temperature above 35° C. for at least about 45 minutes, a second washing step using distilled water, and a third step of acid treatment of hydrogen chloride at between about 1 and 10 Molar concentration at a temperature above 60° C. for at least about 45 minutes. The catalyst is further provided with an additional washing step using distilled water which is then followed by a drying step for at least 4 hours at a temperature above about 105° C. The catalyst is then provided with a calcining step for the catalyst at a temperature above 400° C. for at least about 3 hours. All of the treatment steps of the catalyst are performed prior to oligomerizing the ethylene.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

Figure 1:
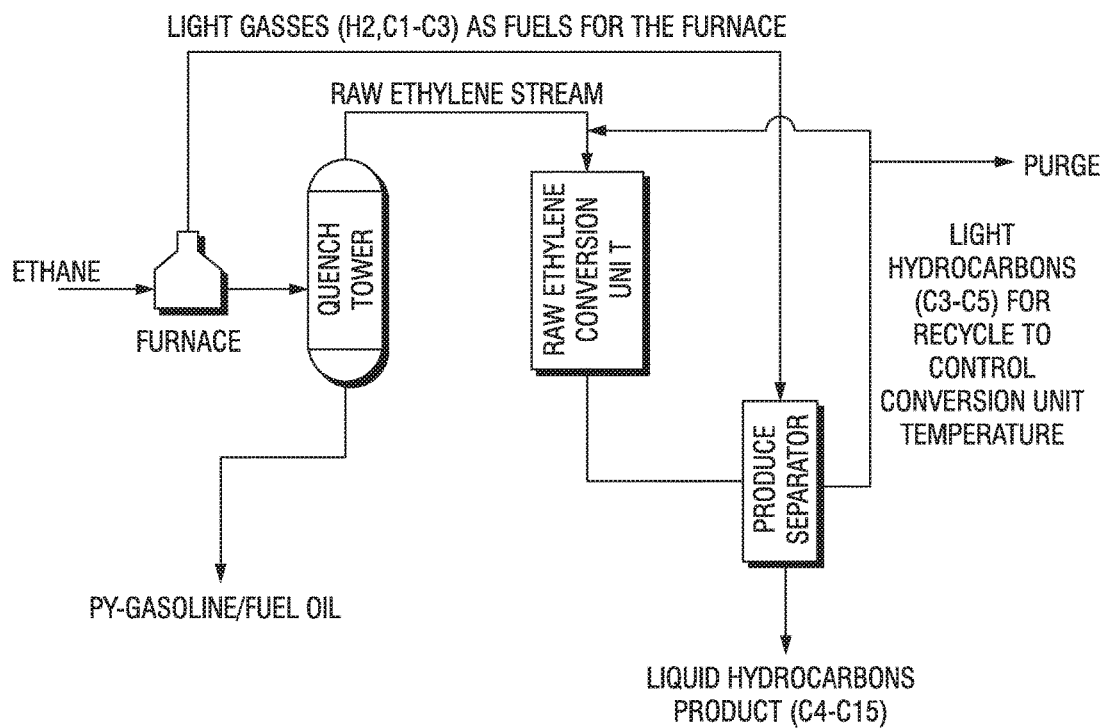
FIG. 1 is a schematic drawing of a reactor for the present invention.

Ethane may be converted to liquid transportation fuel in a process 10 shown schematically in FIG. 1. Ethane from an ethane stream 12 is fed directly into a cracking furnace 14. The process of cracking ethane is typically an uncatalyzed process relying on pressure and temperature in a furnace, such as cracking furnace 14. However, there are catalytic processes for cracking ethane that are acceptable for the present invention. The cracking furnace 14 produces a number products primarily including hydrogen, ethylene, water, methane, and unconverted ethane, but also including small amounts of propylene, acetylene and butadiene, along with trace amounts of other hydrocarbons. All of these products are suitable for conversion in an ethylene oligomerizer in accordance with the present invention.

The products from the cracking furnace 14 are fed directly to a quench tower 16 via a furnace conduit 15 to stop further thermal reactions. A liquid product is taken from the bottom of the quench tower 16 via drain 18 comprising gasoline and fuel oil density materials that may be fed to a refinery. The bulk of the products are vaporous under the conditions in the quench tower 16 and exit the top via overhead conduit 17. The bulk of the products comprise raw ethylene along with the other lighter products described above.

The raw ethylene stream is fed into a catalytic oligomerization reactor 20. The catalytic oligomerization reactor 20 includes a fixed bed of catalyst to convert the raw ethylene stream into a number of products primarily including a gasoline product having an octane rating of about 88. The products from the catalytic oligomerization reactor 20 are conveyed via an outlet conduit to a product separator 22 to separate the products into at least three streams or cuts. A bottom cut comprising a stream of C4 to C15 hydrocarbon molecules that exits the bottom via product conduit 23. These are the valuable products that may be blended into current liquid transportation fuels such as gasoline and perhaps diesel or jet fuel.

The top cut comprises light gases such as hydrogen and C1 to C3 hydrocarbons that are conveyed back to the furnace 14 via light gas conduit 24. These light gases are burned in the furnace 14 to generate heat or supplemental heat for cracking the ethane. A middle cut comprising light hydrocarbons having a C3 to C5 chain length exits middle cut conduit 26. The light hydrocarbons may be recycled to the catalytic oligomerization reactor 20 via recycle conduit 27 or may be purged from the system 10 via purge line 28. If the middle cut is to be purged, it is preferably directed into a refinery stream or to a NGL fractionator for capture and sale.

This process is fairly simple with one well known and well understood unit (the furnace 14), and a second unit (the oligomerization reactor 20) that been considered over the years. Interestingly, in current studies, although there are other products in the feed stream to the catalytic oligomerization reactor 20, in early tests, about 98% of the ethylene was converted and over 75% of the products from the ethylene converted to C5+ materials (Table 1). This is very exciting. With ethane prices depressed and gasoline prices being among the highest priced non-specialty refinery products, this conversion technology could prove to be quite profitable.

The operating conditions may be in a range where the oligomerizing is conducted at a pressure of between 0 psig and 800 psig, the temperature is maintained in a range of between 260° C. and 420° C., and the feed rate measured as a gas hourly space velocity is in a range of between 1000 and 5000 inverse hours. While higher productivity is desired, ideally at least 85% of the ethylene is converted.

So, while this kind of system is exciting, there is a down side. The down side is that although there are quite a number of known catalysts for the catalytic process of oligomerizing ethylene, the catalyst life of these catalysts is desperately short for a financially viable commercial system. Many catalysts have been tested. The best results so far have been accomplished with ZSM-5 catalysts, but the catalyst life of ZSM-5 catalysts still has been measured in hours and has been far shorter than economically viable in a commercial application. While there are many ZSM-5 catalysts produced by many vendors and many have been tested, the productivity and catalyst life tends to vary quite substantially. The basic formulation and sieve structure is the same, but the range of crystallite sizes tend to vary along with the range of catalyst particle sizes, along with the sizes of the micropores and mesopores. There may be many other differences from one manufacturer to another even though the sieve size is quite standardized as set by the crystal structure of alumina and silica and there are no other catalyst metals or materials otherwise added to the ZSM-5 catalyst.

Basically, it is believed that the catalysts tend to coke up pretty fast and while the catalysts may be regenerated through conventional oxidation by burning the coke off the catalyst, such short catalyst life between regeneration cycles will create substantial operating costs. While the current price spread between ethane and gasoline is large and very attractive, price spreads will change over time, most likely shrinking and not expanding. With high operating costs, even a marginal reduction in price spread could substantially reduce or eliminate any profitability of such a commercial system.

TABLE 1

| | |
|---|---|
| Pressure, psig | 50 |
| Temperature, Degrees Celsius | 310 |
| Ethylene conversion, % | 98 |
| HC product selectivity, wt % | |
| | |
| Methane | 0.1 |
| Ethane | 0.8 |
| Propane | 2.1 |
| Propylene | 1.9 |
| Butanes | 9.3 |
| Butenes | 5.5 |
| C5+ | 80.2 |
| | |
| Total, % | 100.00 |

Figure 2:
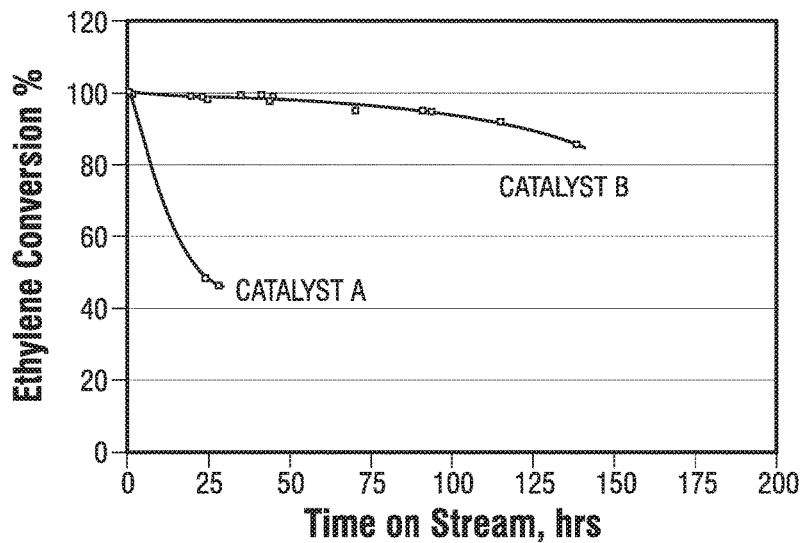
FIG. 2 is a chart showing catalyst life for ethylene conversion in the schematic process according to FIG. 1 for various catalysts.

Focusing on catalyst life, the invention may be illustrated by showing where commercial catalysts A and B were tested in a bench scale reactor at 50 psig and 310° C. High conversion of the ethylene was the focus and as shown in FIG. 2, Catalyst A lost substantial conversion productivity right away while Catalyst B maintained high conversion. However, high conversion for only 100 hours is probably quite a bit short of being suitable for a prospective commercial operation.

Focusing on avoiding coke formation to increase catalyst life, it is believed that the process of forming coke in this reaction system is actually a multistep reaction process that begins with oligomerization, then proceeds to cyclization, then to poly-nuclear cyclization and then finally to coke.

This present invention is focused on doing post synthesis treatments for ZSM-5 catalysts to make them more resistant to coke formation while converting ethylene to liquid hydrocarbon products. So, the ZSM-5 has already been produced by the manufacturer and the inventive process relates to altering the catalyst post production to minimize the production of coke.

Figure 3:
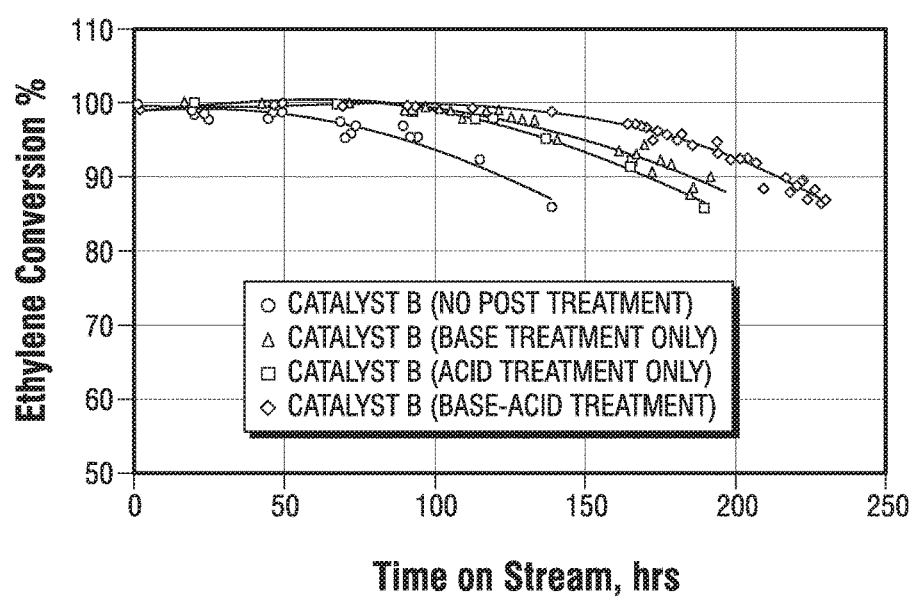
FIG. 3 is a chart showing improved catalyst life over and above that shown in FIG. 2 obtained by the catalyst treatment described in the present invention.

The inventive process comprises a one or two step process for the ZSM-5 catalyst. One process is an acid treatment. As Catalyst B appears to perform better than Catalyst A, the post production efforts are focused on Catalyst B. A sample of Catalyst B is subjected to a 4 Molar concentration HCl (hydrogen chloride) solution for 2 hours at 80° C. The sample is then thoroughly washed again in distilled water and dried at 120° C. for 10 hours. Finally, the sample of Catalyst B (labeled Acid Treated Catalyst B) is calcined at 550° C. for 6 hours. The Acid Treated Catalyst B was tested in a lab scale ethylene conversion process shown in FIG. 1 and the conversion and time on stream are shown in FIG. 3.

Another process is a base treatment. A sample of Catalyst B is exposed to a 0.01 Molar concentration of NaOH (sodium hydroxide) at 40° C. for 0.5 hours. The temperature is raised after the initial 30 minutes to 60° C. to continue for an additional 60 minutes at the same NaOH concentration. The sample is washed in distilled water and dried at 120° C. for 10 hours. Finally, the sample of Catalyst B (labeled Base Treated Catalyst B) is calcined at 550° C. for 6 hours. Base Treated Catalyst B was tested in lab scale ethylene conversion process shown in FIG. 1 and the conversion and time on stream are shown in FIG. 3.

The last process is a two-step process comprising both an acid treatment and a base treatment. A sample of Catalyst B is exposed to a 0.01 Molar concentration of NaOH (sodium hydroxide) at 40° C. for 0.5 hours. The temperature is raised after the initial 30 minutes to 60° C. to continue for an additional 60 minutes at the same NaOH concentration. The sample is washed in distilled water and then subject to an acid wash for 2 hours at 80° C. in a 4 Molar concentration HCl (hydrogen chloride) solution. The sample of Catalyst B (labeled Base-Acid Treated Catalyst B) is thoroughly washed again in distilled water and dried at 120° C. for 10 hours and then calcined at 550° C. for 6 hours. The two step process may be undertaken in either order, but the better results were obtained with the Base treatment being taken first with the Acid treatment second. The Base-Acid Treated Catalyst B was tested in a lab scale ethylene conversion process shown in FIG. 1 and the conversion and time on stream are shown in FIG. 3.

One of the concerns for such treatments was harm to the underlying framework Si/Al ratio. To assess whether the catalyst was being altered in a manner that would reduce the number of regeneration cycles the catalyst could endure, the framework Si/Al ratios were determined by solid-state NMR for each sample. Referring to Table 2 below, the Si/Al ratios are reported for Catalyst B without post treatment, Acid Treated Catalyst B, Base Treated Catalyst B and the Base-Acid Treated Catalyst B. These results suggest that none of the acid treatment, the base treatment or the base-acid treatments have much impact on ZSM-5 framework Si/Al ratios. X-ray diffraction patterns also indicate that the treatments did not destroy the ZSM-5 structure in Catalyst B. Both of these results are unexpected findings. This is probably due to the presence of alumina binder in Catalyst B.

TABLE 2

| Catalyst | Framework Si/Al ratio by NMR |
| --- | --- |
| Catalyst B (without treatment) | 35 |
| Acid treated Catalyst B | 36 |
| Base treated Catalyst B | 39 |
| Base-Acid treated Catalyst B | 38 |

Referring to FIG. 3, it should be appreciated that each of the proposed treatments provide improved catalyst life measurements over Catalyst B without either or both the acid treatment and base treatment in the process described in FIG. 1 and under the same conditions which produced the previously measured catalyst life data shown in FIG. 2. The comparison of the sample catalyst produced conversion productivity and catalyst life data shown in FIG. 3 provides a profound improvement in catalyst life.

The tests were performed under the conditions shown in Table 1 with a representative product slate and performance. These conditions are adequate to compare the stability of the catalysts. For a viable commercial swing fixed bed operation, it is desirable to have about 10 days of catalyst life before it becomes necessary to regenerate the catalyst and at least about a year before replacement of the catalyst becomes necessary, assuming that the catalyst will have undergone many cycles of online production and offline regeneration. The base-acid treated Catalyst B was approaching 10 days online before its ethylene conversion dropped below 90%. This suggests that the minimum target catalyst life for commercial operation is getting close and the inventive process provides a significant step towards that goal. Operational parameters and other developments may further improve catalyst life making the potential commercial operation more economically viable.

It should be recognized that other acids and other base solutions may be used other than HCL and NaOH. And the conditions are not intentionally limited to what is described in the above examples. For example, the base treatment of sodium hydroxide may be in a range of between about 0.001 and about 0.5 Molar concentration although it is anticipated that it might better be in a range of between about 0.005 and about 0.25 Molar concentration or between about 0.0075 and about 0.15 Molar concentration. Similarly, the acid treatment of hydrogen chloride may be in a range of between about 1 and 10 Molar concentration, but might better be in a range of between about 2 and 7 Molar concentration or between about 3 and 5 Molar concentration. As noted, it is preferred that the catalyst be dried and calcined after the acid, base or two step treatment is completed. Drying is preferred at a temperature above 105° C. and calcining is preferred at a temperature above 400° C. The actual treatments may also be preferred at elevated temperatures of between about 35° C. and 90° C.

In closing, it should be noted that the discussion of any reference is not an admission that it is prior art to the present invention, especially any reference that may have a publication date after the priority date of this application. At the same time, each and every claim below is hereby incorporated into this detailed description or specification as additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. An oligomerization process to produce transportation fuels, the process comprising directing a feed stream comprising ethylene to transportation fuel products in a reactor that contains a fixed bed of ZSM-5 catalyst that is essentially free of catalyst metals other than silica and alumina, wherein the ZSM-5 catalyst is supported by an alumina binder, wherein prior to the oligomerization, the ZSM-5 catalyst is provided with a post synthesis treatment comprising an acid wash and a base wash in series to resist coke formation in the zeolite crystallites and extend catalyst life, wherein the oligomerizing is conducted at a pressure between 0 psig and 800 psig, a temperature of between 260° C. and 420° C., and a gas hourly space velocity of between 1000 and 5000 inverse hours and wherein at least 85% of the ethylene is converted.

2. The process according to claim 1 wherein the post synthesis treatment of the catalyst comprises catalyst a base treatment with sodium hydroxide and an acid treatment of hydrogen chloride.

3. The process according to claim 2 wherein the base treatment of sodium hydroxide is at between about 0.001 and about 0.5 Molar concentration.

4. The process according to claim 2 wherein the base treatment of sodium hydroxide is at between about 0.005 and about 0.25 Molar concentration.

5. The process according to claim 2 wherein the base treatment of sodium hydroxide is at between about 0.0075 and about 0.15 Molar concentration.

6. The process according to claim 2 wherein the acid treatment of hydrogen chloride is at between about 1 and 10 Molar concentration.

7. The process according to claim 2 wherein the acid treatment of hydrogen chloride is at between about 2 and 7 Molar concentration.

8. The process according to claim 2 wherein the acid treatment of hydrogen chloride is at between about 3 and 5 Molar concentration.

9. The process according to claim 2 wherein the post synthesis treatment of the catalyst further comprises the steps of drying catalyst and calcining the catalyst after the base-acid treatment.

10. The process according to claim 2 wherein the post synthesis treatment of the catalyst further comprises the steps of drying catalyst at a temperature above 105° C. and calcining the catalyst after the base-acid treatment at a temperature above 400° C.

11. The process according to claim 1 wherein each of the base and acid treatments of the catalyst is done at elevated temperature between 35° C. and 90° C.

12. The process according to claim 11 wherein the base treatment is done first and acid treatment is done second.

13. The process according to claim 1 wherein the base treatment is done first and acid treatment is done second.

14. An oligomerization process to produce transportation fuels, the process comprising directing a feed stream comprising ethylene in a reactor that contains a fixed bed of ZSM-5 catalyst that is essentially free of catalyst metals other than silica and alumina, wherein the ZSM-5 catalyst is supported by an alumina binder, wherein prior to the oligomerization, the ZSM-5 catalyst is treated with a post synthesis treatment to resist coke formation in the zeolite crystallites and extend catalyst life, wherein the oligomerization is conducted at a pressure between 0 psig and 800 psig, a temperature of between 260° C. and 420° C., and a gas hourly space velocity of between 1000 and 5000 inverse hours, wherein at least 85% of the ethylene is converted, wherein the post synthesis treatment of the catalyst comprises a first base treatment with sodium hydroxide at between about 0.0075 and about 0.15 Molar concentration at a temperature above 35° C. for at least about 45 minutes, followed by a washing step using distilled water, followed by an acid treatment using hydrogen chloride at between about 1 and 10 Molar concentration at a temperature above 60° C. for at least about 45 minutes, followed by an additional washing step using distilled water, followed by a drying step for at least 4 hours at a temperature above about 105° C., followed by a calcining step for the catalyst at a temperature above 400° C. for at least about 3 hours.

\* \* \* \* \*